United States Patent
Rose et al.

(10) Patent No.: US 6,709,682 B2
(45) Date of Patent: Mar. 23, 2004

(54) PRODUCT AND METHOD FOR TREATING JOINT DISORDERS IN VERTEBRATES

(75) Inventors: Rebecca Rose, Longmont, CO (US); Gerald L. Chrisope, Boulder, CO (US)

(73) Assignee: In Clover, Inc., Boulder, CO (US)

( * ) Notice: Subject to any disclaimer, the term of this patent is extended or adjusted under 35 U.S.C. 154(b) by 0 days.

(21) Appl. No.: 10/042,815

(22) Filed: Jan. 8, 2002

(65) Prior Publication Data

US 2002/0064568 A1 May 30, 2002

Related U.S. Application Data

(63) Continuation of application No. 09/341,000, filed on Jun. 28, 1999, now Pat. No. 6,344,220, which is a continuation of application No. 08/813,560, filed on Mar. 7, 1997, now Pat. No. 5,916,565.
(60) Provisional application No. 60/013,025, filed on Mar. 8, 1996.

(51) Int. Cl.[7] ................................................ A61K 35/78
(52) U.S. Cl. ...................... 424/756; 424/725; 424/757; 424/760; 424/520; 424/548; 514/62
(58) Field of Search ................................ 424/725, 756, 424/757, 760, 520, 548; 514/62

(56) References Cited

U.S. PATENT DOCUMENTS

| | | | |
|---|---|---|---|
| 3,887,703 A | * | 6/1975 | Manoussos |
| 5,120,538 A | | 6/1992 | Oei |
| 5,364,845 A | * | 11/1994 | Henderson |
| 5,494,668 A | | 2/1996 | Patwardhan |
| 5,587,363 A | | 12/1996 | Henderson |
| 5,916,565 A | * | 6/1999 | Rose et al. |
| 6,344,220 B1 | * | 2/2002 | Rose et al. |

FOREIGN PATENT DOCUMENTS

| | | |
|---|---|---|
| WO | wo 00/44367 | 8/2000 |
| WO | WO 02/09728 A1 | 2/2002 |

OTHER PUBLICATIONS

Castleman; Healing Herbs (1991), Rodale Press: Pennsylvania, pp. 37–39, 186–189, and 355–357.*

Hirschhorn; The Home Herbal Doctor (1982), Parker Publishing Company, Inc.: New York, pp. 50–51.*

Hobbs; Handbook for Herbal Healing (Jan. 1995), Botanica Press: California, pp. 62 and 63.*

Iwu, "Handbooks of African Medicinal Plants", 1993 (CRC Press: Boca Raton, Florida) pp. 139–140.

* cited by examiner

Primary Examiner—Francisco Prats
Assistant Examiner—Susan D. Coe
(74) Attorney, Agent, or Firm—Sheridan Ross P.C.

(57) ABSTRACT

A compound and method of using such compound is disclosed that, when administered to an animal, is capable of arresting the inflammatory response in affected tissues and facilitates the repair and maintenance of damaged tissues in the joints of vertebrates. The combination of natural physiological metabolites and herbal phytochemicals is used to treat connective tissue diseases, the composition preferably orally administered. One embodiment of the composition includes chondroitin sulfate and glucosamine that, when ingested by a vertebrate, suppresses the degradation of connective tissue by an autoimmune response. A preferred composition of the present invention includes a palatability agent, an herbal phytochemical, and a metabolic precursor that synergistically acts to increase blood circulation, thereby enhancing transport of the phytochemical and metabolic precursors to an affected site whereby deleterious inflammatory byproducts are removed.

6 Claims, 3 Drawing Sheets

PRODUCT AND METHOD FOR TREATING JOINT DISORDERS IN VERTEBRATES

CROSS REFERENCE TO RELATED APPLICATIONS

The present application is a continuation of U.S. patent application Ser. No. 09/341,000 filed Jun. 28, 1999 now U.S. Pat. No. 6,344,220, which is a continuation from U.S. patent application Ser. No. 08/813,560 filed Mar. 7, 1997, now U.S. Pat. No. 5,916,565, which claims priority from U.S. Provisional Application Ser. No. 60/013,025, filed Mar. 8, 1996.

FIELD OF THE INVENTION

The present invention is directed to compounds, and methods using such compounds, that when administered to an animal, arrest the inflammatory response in affected tissues and facilitate repair and maintenance of damaged tissues in the joints of vertebrates.

BACKGROUND OF THE INVENTION

In healthy conditions, articular cartilage forms a smooth surface between articulating bone ends to reduce the friction caused by movement. This friction is further reduced by the synovial fluid.

Articular cartilage consists of chondrocytes and two major macro-molecules; i.e., collagen and proteoglycans, which are synthesized by and deposited around the chondrocytes. The chondrocytes also synthesize the synovial fluid which bathes the articular cartilage.

The structural integrity of the articular cartilage is the foundation of optimal functioning of the skeletal joints in the hip, shoulders, elbows, hocks and stifles. Impaired function of skeletal joints will dramatically reduce mobility such as rising from sitting position or climbing and descending stairs.

To maintain the structural integrity and the proper functioning of the articular cartilage, the chondrocytes constantly synthesize collagen and proteoglycans, the major components of the articular cartilage, as well as the friction-reducing synovial fluid. This constant synthesis of the macro-molecules and synovial fluid provides the articular cartilage with the repairing mechanism for most of the wearing caused by friction between the bone ends. However, it also leads to the constant demand for the supply of precursors, or building blocks, for the macromolecules and synovial fluid. Lack of this precursors will lead to defects in the structure and function of the skeletal joints. This deficiency occurs often when activity levels are very high, or cartilage tissue has been traumatized.

An adequate supply of metabolic precursors or building blocks is thus paramount to replacement and repair of the constituents of skeletal joints, connective tissue and synovial fluid. Proteoglycans (or mucopolysaccharides) form the ground substance of cartilage, bone and joint fluid. Proteoglycans are comprised of proteins linked to glycosaminoglycans (GAGS). The building block GAG subunit of the proteoglycan in cartilage and bone is chondroitin sulfate. Chondroitin sulfate A is present in cornea and cartilage. Chondroitin sulfate B (G-heparin) is found in tendon, aorta, skin and heart valves. Chondroitin C is found in cartilage, tendon and umbilical cord and similar tissues. The building block GAG subunit of the proteoglycan in joint fluid is hyaluronic acid. Intercellular solutions of hyaluronic acid are viscous and thus assist in lubrication of the joints of body skeleton. Hyaluronic acid is synthesized from the metabolic precursor, glucosamine. The availability of glucosamine in cartilage tissue can be rate-limiting to the enzymatic step leading to the production of proteoglycans. Exogenous glucosamine serves to drive the biosynthetic pathway forward past the rate-limiting blockage point. Glucosamine serves as a substrate for a kinase enzyme which yields glucosamine-6-phosphate, the rate-limiting precursor in proteoglycan synthesis. Recently, studies have reported the suppression of autoimmune disorders such as rheumatoid arthritis upon ingestion of cartilage fibers derived from chickens and sharks. The therapy, termed oral tolerization, is not fully understood but it is theorized that a mechanism in the digestive tract disarms immune cells that would otherwise assault food molecules as foreign intruders to the body, akin to foreign substances that enter the blood stream by means other than the gastrointestinal tract. Apparently, the immune-disarming effect occurs not only in the gut, but also in the vulnerable tissues.

Numerous disclosures describe therapy of damaged tissues by introduction of precursors in the metabolic pathway leading to biosynthesis of the macromolecules of connective tissues. For example, in U.S. Pat. No. 3,697,652 (Rovati et al.), N-acetylglucosamine is used to treat degenerative afflictions of the joints. In U.S. Pat. No. 3,683,076 (Rovati et al.), glucosamine salts are described as pharmaceutically useful for treatment of osteoarthritis and rheumatoid arthritis. U.S. Pat. Nos. 4,647,453 (Meisner) and 4,772,591 (Meisner) disclose the use of glucosamine salts for treatment of degenerative inflammatory disease and as a means of accelerating wound healing. In U.S. Pat. No. 4,801,619 (Lindblad), a hyaluronic acid preparation is claimed to be effective for treatment of steroid arthropathy and progressive cartilage degeneration caused by proteoglycan degradation. A combination of glucosamine, chondroitin and manganese is claimed in U.S. Pat. No. 5,364,845 (Henderson) as a means of protecting and repair of connective tissue. None of these prior investigators, however, disclose a composition having metabolic precursors, herbal phytochemicals and palatability agents that work synergistically to prevent and treat joint and connective tissue disorders.

SUMMARY OF THE INVENTION

The present invention relates to prophylaxis and therapy of joint disorders in vertebrates accomplished by oral administration of a combination of natural physiological metabolites and herbal phytochemicals. Arthritic disorders, including rheumatism, osteoarthritis, dysplasia, lupus, bursitis and gout, are all characterized by inflammation and pain in joints, muscles and related connective tissues. Most of the forms are progressive. The present inventors disclose for the first time herein a synergistic effect of the natural physiological metabolites and herbal phytochemicals for treatment of joint disorders in vertebrates.

The present invention is directed to a composition capable of eliminating or diminishing inflammation are in accelerating the tissue repair process. Even though prior investigators used anti-inflammatory substances, their compositions did not provide a complete array of necessary repair and maintenance precursor building blocks along with anti-inflammatory substances. Furthermore, the anti-inflammatory substances utilized by prior investigators are not comprised of natural herbal phytochemicals. In fact, it is known that some substances which exhibit anti-inflammatory responses, such as glucosamine, do not exert general activity. Instead, the response may be mediator specific. Thus, one aspect of the present invention relates to the provision of multiple anti-inflammatory herbal phytochemicals that have more general reactivity and, hence, are more efficacious in a broader population.

One aspect of the present invention relates to a composition of chondroitin sulfate and glucosamine to provide the necessary building blocks and biosynthetic regulation for repair and maintenance of cartilage, bone, tendon and joint lubricating fluids. It is believed that ingestion of cartilage or connective tissue precursor building blocks such as chondroitin may elicit the same oral tolerance effects, thus suppressing the degradation of connective tissue by an autoimmune response. For chondroprotective agents such as chondroitin sulfate and glucosamine to be efficacious when orally administered, it is important that they be absorbed from the intestinal tract without change in their chemical structure. Studies have confirmed that both chondroitin sulfate and glucosamine are absorbed without modification of their molecular structure.

The present invention is also directed to the use of antioxidants in the control of inflammation and its degradative effects on connective tissue. Oxygen-derived free radicals apparently act as mediators of inflammation and/or tissue destruction in inflammatory and arthritic disorders. Free radicals degrade synovial fluid hyaluronic acid, modify collagen and perhaps proteoglycan structure and/or synthesis, alter and interact with immunoglobulins, activate degradative enzymes and inactivate their inhibitors, and possibly participate in chemotaxis. The present invention thus relates to a composition containing antioxidants that are advantageous in that the free radicals are scavenged and detoxified before they reach the affected area.

Prior investigators also failed to disclose a means of increasing circulation to the affected area. The present invention therefore relates to increasing circulation to accelerate the repair process by removal of deleterious inflammatory substances and by providing copious quantities of precursor building blocks for repair and maintenance.

One aspect of the present invention is directed to compositions containing ingredients that enhance the absorption of necessary repair precursors from the gastrointestinal tract. Another aspect relates to a means of enhancing the oral palatability of such composition. Clearly, compliance is necessary to ensure proper dosage of active ingredients necessary for therapeutic functions. Ingestion of the total dosage regimen is even more dependent on palatability in animals who only voluntarily consume oral compositions if they are presented with an acceptable flavor.

Therefore, the present invention is intended to provide a means of accelerating the repair of arthritic tissues by provision of metabolic precursor building blocks, herbal phytochemicals and palatability agents. This combination has synergistic advantages over previously known compositions. As disclosed in more detail in the detailed description of the invention and the appended figures, the present invention provides a composition and method for treating various joint disorders in vertebrates utilizing the synergistic combination of natural physiological metabolites and herbal phytochemicals, together with palatability agents.

DETAILED DESCRIPTION

Figure 1:
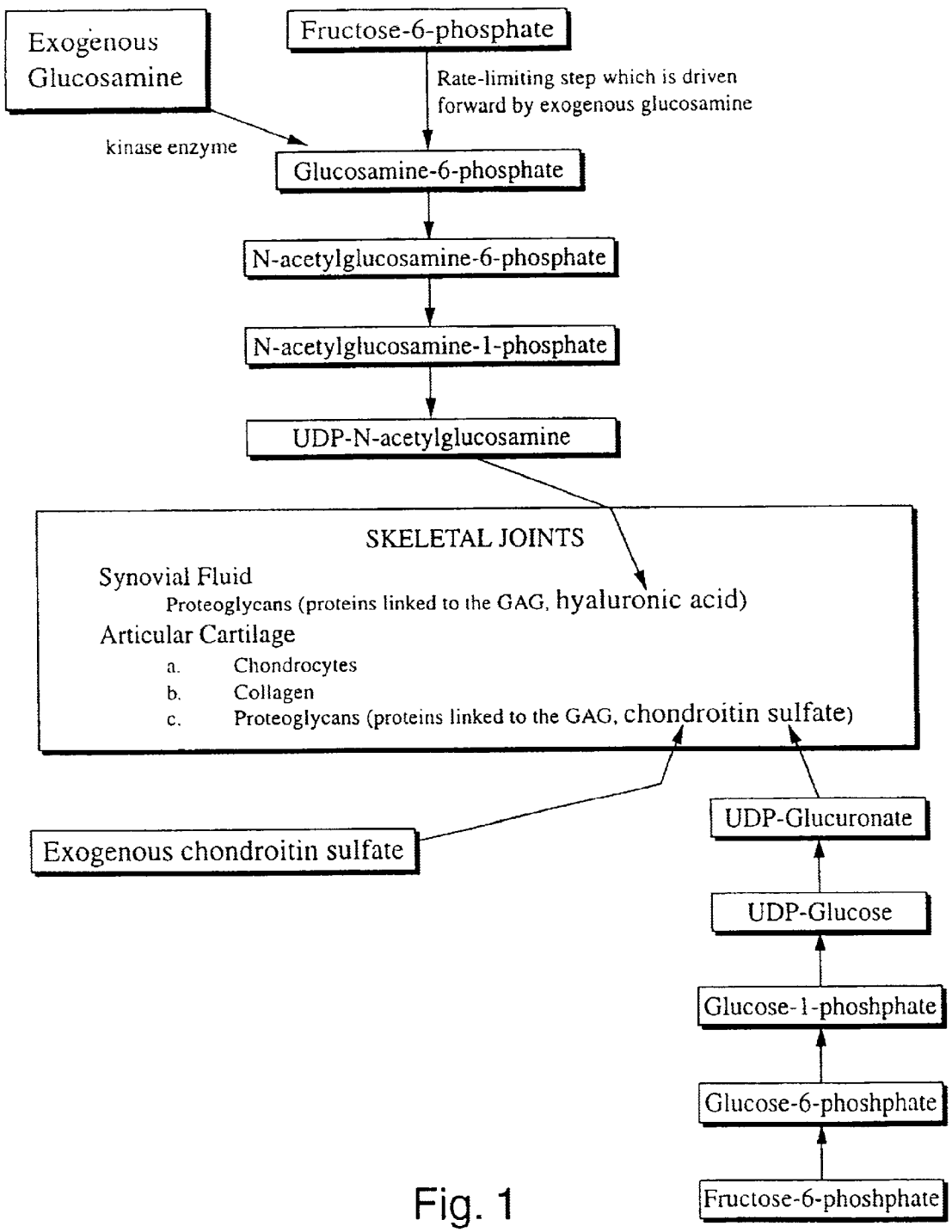
FIG. 1 portrays the metabolic pathways leading to the biosynthesis of macromolecules of connective tissue and synovial fluid.

The present invention discloses an orally administered composition of metabolic precursors, herbal phytochemicals and palatability agents capable of prophylaxis and therapy of joint and connective tissue disorders in vertebrates. The components of the composition act synergistically to encourage dosage compliance by provision of flavorful palatability agents; to provide sufficient sources of necessary metabolic precursors for repair and maintenance of connective tissues; to ensure the proper absorption of these metabolic precursors in the digestive tract; to diminish the inflammatory response in the affected area so that the connective tissue degradation process is halted and repair may be initiated; to suppress the autoimmune response which creates the inflammatory response and further degrades tissue in the affected area; and to stimulate the blood circulatory system which simultaneously enhances the delivery of the metabolic precursors to the affected areas and removes deleterious deposits in the affected areas.

One embodiment of the present invention relates to a composition for treating joint disorders in vertebrates. Such a composition includes a palatability agent, an herbal phytochemical and a metabolic precursor. The palatability agent, the phytochemical and the metabolic precursor act synergistically to increase blood circulation, thereby enhancing transport of the phytochemical and metabolic precursor to an affected site whereby deleterious inflammatory byproducts are removed.

Palatability Agents

The palatability agents of this composition serve to add flavor to the composition so that an effective dosage is most likely to be ingested. It is within the scope of the present invention that any safe, flavor enhancing palatability agent can be used in a composition of the present invention. Particularly suitable palatability agents for use in the composition of the present invention include, but are not limited to, plant oils, plant hydrolysates, yeast, yeast hydrolysates, and organ and muscle preparations derived from fowl, bovine, porcine or fish.

The individual functions of the metabolic precursors and herbal phytochemicals of the composition of the present invention are described hereafter:

Metabolic Precursors

In one embodiment of the present invention, suitable metabolic precursors for use in a composition of the present invention include, but are not limited to glucosamine, glucosamine salts, chondroitin sulfate, mucopolysaccharides and tissue preparations containing chondroitin sulfate.

1. Chondroitin sulfate in a purified state or as a component of bovine tracheal extract/powder: Chondroitin sulfate is a major component of cartilage. It stimulates the regeneration of damaged cartilage tissues. Additionally, it has a lubricating effect on joint cavities with a positive effect on synovial fluid viscosity. More specifically, proteoglycans (or mucopolysaccharides) form the ground substance of cartilage, bone and joint fluid. Proteoglycans are comprised of proteins linked to glycosaminoglycans (GAGs). The building block GAG subunit of the proteoglycan in cartilage and bone is chondroitin sulfate. Chondroitin sulfate A is present in cornea and cartilage. Chondroitin sulfate B (G-heparin) is found in tendon, aorta, skin and heart valves. Chondroitin C is found in cartilage, tendon and umbilical cord and similar tissues. Thus, an adequate supply of metabolic precursors or building blocks is paramount to replacement and repair of the constituents of skeletal joints, connective tissue and synovial fluid. Additionally, it is possible that ingestion of cartilage or connective tissue precursor building blocks such as chondroitin may elicit an oral tolerance effect, thus suppressing the degradation of connective tissue by an autoimmune response.

In one embodiment of the present invention, chondroitin sulfate is derved from bovine tracheal digest. This digest includes mucopolysaccharides and tissue preparations containing chondroitin sulfate.

2. Glucosamine and its salts: Glucosamine is another precursor building block of articular cartilage. The building block GAG subunit of the proteoglycan in joint fluid is hyaluronic acid. Intercellular solutions of hyaluronic acid are viscous and thus assist in lubrication of the joints of body skeleton. Hyaluronic acid is synthesized from the metabolic precursor, glucosamine. The availability of glucosamine in cartilage tissue can be rate-limiting to the enzymatic step leading to the production of proteoglycans. Exogenous glucosamine serves to drive the biosynthetic pathway forward past the rate-limiting blockage point. Apparently, glucosamine serves as a substrate for a kinase enzyme which yields glucosamine-6-phosphate, the rate-limiting precursor in proteoglycan synthesis.

Hence, a composition of chondroitin sulfate and glucosamine provides the necessary building blocks for repair and maintenance of cartilage, bone, tendon and joint lubricating fluids.

According to the present invention, when a metabolic precursor included in a composition for treating joint disorders is glucosamine, the daily dose for vertebrates is preferably from about 50 mg to about 2000 mg of glucosamine per 25 pounds of body weight. When a metabolic precursor included in a composition for treating joint disorders is chondroitin sulfate mucopolysaccharide, the daily dose for vertebrates is preferably from about 50 mg to about 2000 mg of chondroitin sulfate mucopolysaccharide per 25 pounds of body weight.

Herbal Phytochemicals

In one embodiment, a suitable herbal phytochemical for use in a composition of the present invention includes, but is not limited to cayenne, ginger, turmeric, yucca, Devil's Claw, nettle leaf, Black Cohosh, alfalfa and celery seeds.

Some herbal phytochemicals in the composition have similar or identical functions but the mechanisms employed to achieve the functions may differ. This overlap of functions is advantageous in that individuals often respond differently to a single chemical. Also, the response of an individual may vary based on his environmental and physiological conditions at the time of therapy. Hence, a multiplicity of phytochemicals with similar functions accommodates diversity within and among individuals and populations. It is likely that this multiple component approach is one reason this invention demonstrates faster and greater levels of efficacy than prior art inventions. Of course, another reason for enhanced efficacy is the synergy provided by having a complete array of functional ingredients in one composition.

1. Cayenne: Cayenne contains the phytochemical, capsaicin. Capsaicin stimulates the release of a neurotransmitter called substance P which alerts the brain of pain with subsequent inflammatory response in the affected area. Overstimulated release of substance P by capsaicin eventually depletes the supply of substance P thus reducing the pain signal to the brain. This desensitization diminishes inflammation, a beneficial effect since continued inflammation in joints increases cartilage breakdown and delays the repair mechanisms.

Cayenne is also a stimulator of the circulatory system, resulting in increased blood supply to tissues. Increased blood supply serves the dual beneficial roles of removing detrimental inflammatory by-products such as free radicals and transporting an ample supply of anti-oxidants and metabolic precursor building blocks for repair.

According to the present invention, when the herbal phytochemical included in a composition for reating joint disorders is cayenne, the daily dose for vertebrates is preferably from about 2 mg to about 55 mg of cayenne per 25 pounds of body weight.

2. Ginger root: Ginger functions as a circulatory stimulant to relax peripheral blood vessels thus serving the dual beneficial roles of removing detrimental inflammatory byproducts such as free radicals and transporting an ample supply of anti-oxidants and metabolic precursor building blocks for repair.

Ginger also functions as an antioxidant. Oxygen-derived free radicals apparently act as mediators of inflammation and/or tissue destruction in inflammatory and arthritic disorders. Free radicals degrade hyaluronic acid, modify collagen and perhaps proteoglycan structure and/or synthesis, alter and interact with immunoglobulins, activate degradative enzymes and inactivate their inhibitors, and possibly participate in chemotaxis. It is reasonable to conclude that a composition containing antioxidants would be advantageous in that the free radicals could be scavenged and detoxified before they reached the affected area.

Additionally, some studies report that ginger is useful as a digestive aid.

According to the present invention, when the herbal phytochemical included in a composition for treating joint disorders is ginger or ginger root, the daily dose for vertebrates is preferably from about 50 mg to about 220 mg of ginger or ginger root per 25 pounds of body weight.

3. Turmeric: Turmeric has been shown to possess antioxidant properties. Dietary turmeric lowers lipid peroxidation by enhancing the activities of antioxidant enzymes. Antioxidant activities diminish free radicals which aggravate the inflammatory response.

According to the present invention, when the herbal phytochemical included in a composition for treating joint disorders is turmeric, the daily dose for vertebrates is preferably from about 50 mg to about 400 mg of turmeric per 25 pounds of body weight.

4. Yucca: Yucca supplies saponins, a group of steroid derivatives which serve as the precursors in the synthesis of cortisone and related corticoids. Numerous studies of saponin extracts have reported relieve of arthritic symptoms such as swelling and pain.

According to the present invention, when the herbal phytochemical included in a composition for treating joint disorders is yucca, the daily dose for vertebrates is preferably from about 400 mg to about 3000 mg of yucca per 25 pounds of body weight.

5. Devil's Claw: Devil's Claw is anti-inflammatory, analgesic, sedative, diuretic and antirheumatic. It also serves as a liver stimulant. It can be extremely effective in certain conditions.

According to the present invention, when the herbal phytochemical included in a composition for treating joint disorders is Devil's Claw, the daily dose for vertebrates is preferably from about 200 mg to about 2000 mg of Devil's Claw per 25 pounds of body weight.

6. Nettle leaf: Nettle leaf stimulates circulation. It is also used as a blood purifier and diuretic. This function results in the removal of detrimental inflammatory by-products out of the circulatory system. It is especially useful in treating gout by removing uric acid from circulation.

According to the present invention, when the herbal phytochemical included in a composition for treating joint disorders is nettle leaf, the daily dose for vertebrates is preferably from about 100 mg to about 750 mg of nettle leaf per 25 pounds of body weight.

7. Black Cohosh: Black Cohosh has peripheral vasodilatory and anti-inflammatory effects. It has been reported as a remedy for rheumatism and relieves pain and irritation.

According to the present invention, when the herbal phytochemical included in a composition for treating joint disorders is Black Cohosh, the daily dose for vertebrates is preferably from about 20 mg to about 500 mg of Black Cohosh per 25 pounds of body weight.

8. Alfalfa: The anti-rheumatic effect of alfalfa is reportedly due to its nutritive content of vitamins A, B1, B6, B12, C, E3 K, niacin, pantothenic acid, biotin, folic acid, and saponins.

According to the present invention, when the herbal phytochemical included in a composition for treating joint disorders is alfalfa, the daily dose for vertebrates is preferably from about 100 mg to about 800 mg of alfalfa per 25 pounds of body weight.

9. Celery Seeds: Celery seeds are used in the treatment of gout and rheumatism. They function as an anti-inflammatory agent and diuretic.

According to the present invention, when the herbal phytochemical included in a composition for treating joint disorders is celery seeds, the daily dose for vertebrates is preferably from about 20 mg to about 400 mg of celery seeds per 25 pounds of body weight.

Composition

Thus, the inventors have discovered a synergy with the ingredients of the composition which may be broadly summarized as:

1. Palatability agents increase likelihood that an adequate dose of the composition will be consumed.
2. Herbal phytochemicals act in accompaniment to enhance absorption of ingredients, increase circulation to carry nutrients to affected tissues, increase circulation to remove deleterious substances in the affected tissues, decrease inflammation, and diminish damaging effects of free radicals by antioxidative action.
3. Metabolic precursors for biosynthesis of macromolecules necessary for repair and maintenance of the damaged tissues in the joints.

Figure 2:
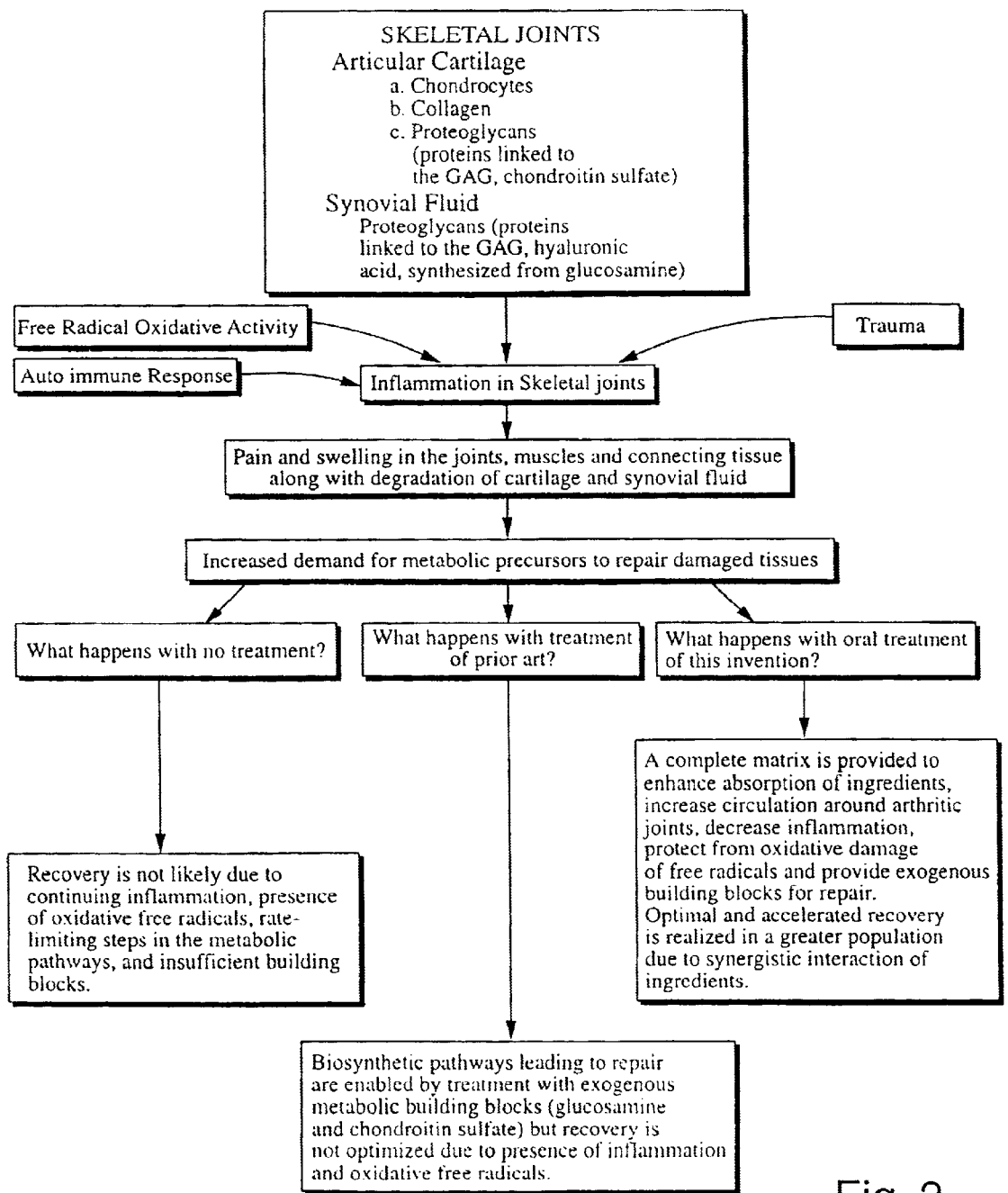
FIG. 2 is a diagram showing various advantages offered by the present invention over the absence of treatment and over conventional therapy of joint disorders.

The sequential functions of the 3 groups of ingredients in the composition results in accelerated repair of connective tissues in the joint areas. FIG. 2 illustrates the synergistic functions of the combination which are novel as a composition and as a combined means of providing a multiplicity of prophylactic and therapeutic mechanisms to a wide population of biologically diverse individuals.

In one embodiment of the present invention, a composition for treating joint disorders in vertebrates has a flavor that is desirable to a vertebrate to be treated.

In another embodiment, the composition arrests the inflammatory response in an affected tissue, thereby permitting degradation processes to be halted and repair to be initiated.

In yet another embodiment, the composition diminishes the oxidative effects of free radicals and precludes damage to anabolic enzymes used in the metabolic synthesis of components required to repair damaged tissues.

In yet another embodiment, the composition of the present invention precludes the degradation of synovial fluid hyaluronin.

In another embodiment, the composition of the present invention suppresses an autoimmune response in a vertebrate.

Another embodiment of the present invention includes a composition for treating joint disorders in vertebrates. The composition includes:

(a) a palatability agent which can include yeast, yeast autolysates, and/or organ and muscle preparations derived from chicken or bovine;

(b) an herbal phytochemical which can include cayenne, ginger, turmeric, yucca, Devil's Claw, nettle leaf, Black Cohosh, alfalfa and/or celery seeds; and (c) a metabolic precursor which can include glucosamine, glucosamine salts, chondroitin sulfate, mucopolysaccharides and/or tissue preparations containing chondroitin sulfate. The daily dose of such a composition includes from about 50 to about 2000 mg of the metabolic precursor per 25 pounds of body weight, and from about 2 to about 3000 mg of the phytochemical per 25 pounds of body weight.

Yet another embodiment of the present invention relates to a method for treating joint disorders in vertebrates. Such a method includes the step of administering to a vertebrate a therapeutically effective quantity of a palatability agent, an herbal phytochemical and a metabolic precursor. The composition preferably includes effective quantities of cayenne, ginger, turmeric, yucca, Devil's Claw, nettle leaf, Black Cohosh, alfalfa, celery seeds, glucosamine and salts thereof, and chondroitin sulfate. Such a composition is effective to increase blood circulation in a vertebrate. In a further embodiment, the composition used in such a method has an effect which can include arresting an inflammatory response, diminishing the oxidative effect of free radicals, suppressing an autoimmune response and/or providing metabolic precursors for biosynthesis of macromolecules necessary in the repair and maintenance of damaged joint tissues.

The composition of the present invention can be administered to any vertebrate animal, preferably mammals, and even more preferably pets, such as dogs, cats, etc. Acceptable protocols to administer the composition in an effective manner include individual doses, number of doses, frequency of dose administration, and mode of administration. Modes of delivery can include any method compatible with prophylactic or treatment of a disease. The preferred mode of delivery is through oral administration of the composition. Those of skill in the art will appreciate the number, frequency and amount of dosage sizes for any particular situation.

According to the present invention, an effective quantity of a component of a composition of the present invention to administer to a vertebrate comprises an amount that is capable of alleviating a joint disorder, without being toxic to the vertebrate. An amount that is toxic to a vertebrate comprises any amount that causes damage to the structure or function of a vertebrate (i.e., poisonous).

The following examples are provided for the purposes of illustration and are not intended to limit the scope of the present invention.

EXAMPLES

The following case studies with dogs indicate that this composition is not only efficacious but provides accelerated therapy over prior art.

Example 1

Case Study #1

A 112 pound twelve-year-old Shepherd cross presented with stiffness and a limp since 1 year old. Preliminary diagnosis was hip dysplasia and shoulder arthritis. The dog was first placed on recommended dose of Cosequin (U.S. Pat. No. 5,364,845 —Henderson) for 3 months. only minor improvement in symptoms were observed after 1 month on Cosequin. Treatment was switched to 8 teaspoons of the present invention for 2 weeks, The dog's symptoms improved significantly within 4–5 days. The veterinarian reported a 60–70% relief of symptoms after 2 weeks. The owner feels that the present invention is more efficacious than the prior treatment because relief occurred faster. The owner does not hear crepitus when the dog walks up stairs. The dog still limps but has more energy and plays more. The dog is currently well and is on a maintenance dose of 4 teaspoons daily.

Example 2

Case Study #2

A 100 pound ten-year-old Labrador Retriever with stiff back legs had difficulty rising from a prone position and demonstrated limited movement. The dog tore his anterior crucia (knee) when he was 5-years-old and developed serious arthritis after being misdiagnosed. The owner tried "everything": Adequan (a 25% aqueous solution of a polysulfated glycosaminoglycan, injectable), massage, acupuncture, etc. Nothing worked. After the dog was on 8 teaspoons of the present invention daily, improvement was observed within 24 hours; i.e., after only one dose. Remarkable improvement was noticed when the dog has been on the present invention for 3 days. The dog's quality of life has improved 80%, according to the owner. The dog is currently maintained on a 4-teaspoon daily dose and is doing well. He can rise and run easily. The stiffness is almost not noticeable. The owner has taken the dog off Ascriptin, an aspirin-containing pain reliever, for the first time in 5 years and has not observed any pain or limited movement.

Figure 3:
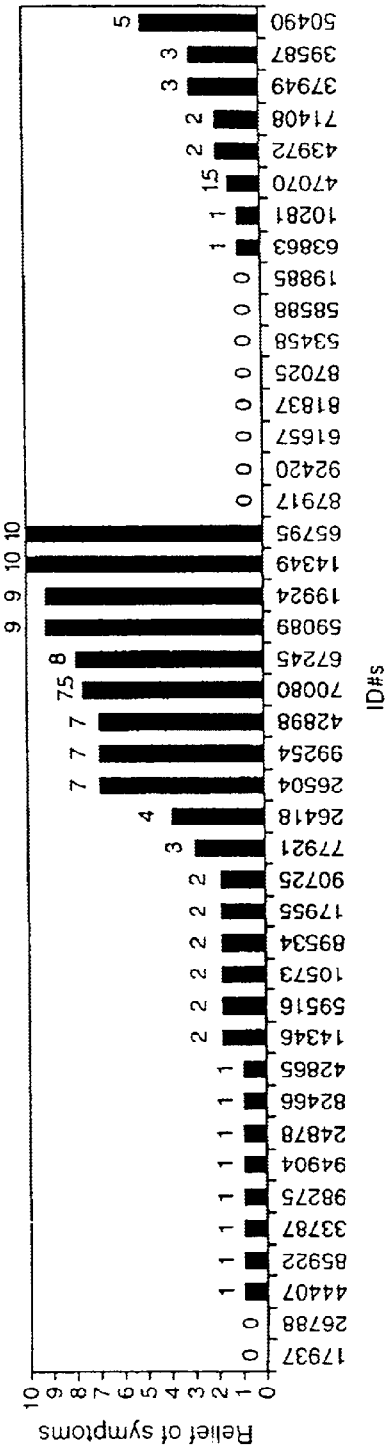
FIG. 3 is a table showing the combined results of placebo-controlled, double-blinded clinical trials with dogs in New York state and Colorado.

Placebo-controlled, double-blinded clinical studies with dogs were conducted to further demonstrate the efficacy, safety and palatability of an arthritis treatment using herbal phytochemicals and natural chondroprotective agents. A controlled experimental design was used to avoid reliance on mere anecdotal testimonies as evidence of efficacy. Privately owned adult dogs, greater than 1 year old, of any breed and either sex, with a clinical evidence of joint discomfort were considered for inclusion in the study. Primary diagnosis of joint discomfort was made on the basis of clinical and historical signs and after a physical examination by a licensed veterinarian. Dogs were excluded from the trial if they were pregnant, were medically ill or if joint discomfort was a result of an existing neurologic, immunologic or neoplastic condition. Forty-three dogs met the criteria and were included in the study. Twenty-seven dogs received the active test composition and sixteen dogs received the placebo composition. The population included sexually intact males, castrated males, sexually intact females and spayed females. Mean SD age of the dogs was 5.5±3.4 years. There were no significant differences between the test and control groups in the ages, sexes and body weights. The most common sites for joint disorders were the coxofemoral, stifle and elbow joints. Clinical signs included lameness, stiffness after rising, signs of pain, crepitating when the affected joint was palpated, decreased range of motion in the affected joint and muscle atrophy. Dogs included in the study were randomly assigned to receive the active test composition or placebo for 14 days. Neither the investigators, nor the owners, nor the veterinarians knew which composition was being administered to each dog. Before the administration of the compositions, a complete physical examination was performed on each dog, and blood samples were obtained for CBC and serum biochemical analyses (which included glucose, creatinine, total protein, albumin, total bilirubin, alkaline phosphatase, ALT, AST, lactic dehydrogenases, cholesterol, calcium, phosphorous, sodium, potassium, chloride and globulin). The physical examination was repeated by the veterinarians on the eighth day after the administration was initiated and improved mobility was assessed by the veterinarians on a 0 to 10 scale with 0 as no relief and 10 as complete relief. Physical examinations, CBC and serum biochemical analyses were repeated on the fifteenth day after the first administration of the composition. FIG. 3 is a table portraying combined data from both studies comparing levels of recovery in dogs receiving placebos and in dogs receiving active test product.

The statistical analysis provided in the table of FIG. 3 confirms that the symptoms of the study group were significantly improved when compared with the control group. Indeed, a P value of 0.05 is considered statistically significant. The P value of this study was 0.0064 indicating that the probability that the test and control groups are different is 99.36%. No adverse reactions were reported. The serum chemistry analyses did not show any significant toxic effects.

Example 3

This example shows the ingredients in a composition for treating joint disorders of the present invention. For each active ingredient listed below, the amount given is equivalent to about a one month supply effective to treat a 50 pound dog. The ingredients are blended in a ratio of 60% active ingredients to 40% palatability enhancer. The palatability enhancer consists of hydrogenated vegetable oils and beef extract.

Active ingredients: cayenne pepper (0.28 g); turmeric (8.4 g); ginger root (5.6 g); Black Cohosh (2.8 g); Yucca root (56 g); Devil's Claw (28 g); nettle leaf (16.8 g); alfalfa leaf (28 g); celery seed (2.8 g); D-glucosamine HCL (28 g) and mucopolysaccharides (78.4 g).

The foregoing description of the invention has been presented for purposes of illustration and description. Further, the description is not intended to limit the invention to the form disclosed herein. Consequently, variations and modifications commensurate with the above teachings, and the skill or knowledge in the relevant art, are within the scope of the present invention. The preferred embodiment described hereinabove is further intended to explain the best mode known of practicing the invention and to enable others skilled in the art to utilize the invention in various embodiments and with various modifications required by their particular applications or uses of the invention. It is intended that the appended claims be construed to include alternate embodiments to the extent permitted by the prior art.

What is claimed is:

1. A composition for the treatment of arthritis, joint stiffness, joint mobility and joint pain in vertebrates, based on 25 pounds of body weight, comprising from about 2 to 55 mg of cayenne, from about 50 to 220 mg of ginger, from about 50 to 400 mg of turmeric, from about 400 to 3000 mg of yucca, from about 200 to 2000 mg of Devil's Claw, from about 100 to 750 mg of nettle leaf, from about 20 to 500 mg of black cohosh, from about 100 to 800 mg of alfalfa, from about 20 to 400 mg of celery seeds, from about 50 to 2000 mg of D-glucosamine HCl: and from about 50 to 2000 mg of mucopolysaccharides.

2. The composition of claim 1, wherein the vertebrate is selected from the group consisting of a dog, a horse and a cat.

3. The composition of claim 1, wherein said composition has a flavor desirable to the vertebrate to be treated.

4. The composition of claim 1, wherein said composition diminishes the oxidative effect of free radicals in joints.

5. The composition of claim 1, wherein said composition diminishes the degradation of synovial fluid hyaluronin in joints.

6. The composition of claim 1, wherein said composition suppresses the immune response of said vertebrate.

* * * * *